United States Patent [19]
Wilhelm et al.

[11] Patent Number: 5,466,697
[45] Date of Patent: Nov. 14, 1995

[54] 8-PHENYL-1,6-NAPHTHYRIDIN-5-ONES

[75] Inventors: Robert S. Wilhelm, Mountain View; Bradley E. Loe, Santa Cruz, both of Calif.

[73] Assignee: Syntex (U.S.A.) Inc., Palo Alto, Calif.

[21] Appl. No.: 274,615

[22] Filed: Jul. 13, 1994

[51] Int. Cl.$^6$ ............ A61K 31/435; C07D 471/04
[52] U.S. Cl. .................................. 514/300; 546/122
[58] Field of Search ..................... 546/122; 514/300

[56] References Cited

U.S. PATENT DOCUMENTS 4,698,341  10/1987  Satzinger et al. ............. 514/230

FOREIGN PATENT DOCUMENTS 8431299  1/1985  Australia.
2054593  2/1981  United Kingdom.

*Primary Examiner*—Bernard Dentz
*Attorney, Agent, or Firm*—Rohan Peries

[57] ABSTRACT

The disclosed 8-aryl-1,6-naphthyridin-5-ones, compounds of Formula I,

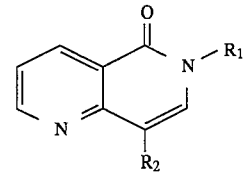

wherein:

$R_1$ is hydrogen, alkyl, lower alkyl, cycloalkyl, heteroalkyl, heterocycloalkyl, aryl, heteroaryl, cycloalkyl lower alkyl, heterocycloalkyl lower alkyl, aralkyl or heteroaralkyl; and $R_2$ is aryl; or a pharmaceutically acceptable salt or N-oxide thereof are useful as anti-inflammatory agents, immunosuppressive agents, anti-allograft rejection agents, anti-graft-vs-host disease agents, anti-allergic agents (e.g., asthma, rhinitis and atopic dermatitis), bronchodilation agents, anti-autoimmune agents or analgetic agents.

29 Claims, No Drawings

8-PHENYL-1,6-NAPHTHYRIDIN-5-ONES

BACKGROUND OF THE INVENTION

1. Field of the Invention

This invention relates to derivatives of 8-aryl-1,6-naphthyridin- 5-ones useful as anti-inflammatory agents, immunosuppressive agents, anti-allograft rejection agents, anti-graft-vs-host disease agents, anti-allergic agents (e.g., asthma, rhinitis and atopic dermatitis), bronchodilation agents, anti-autoimmune agents or analgetic agents, to their precursors, to their preparation and to pharmaceutical compositions using the compounds of the invention.

2. Background Information

Cyclic 3', 5'-adenosine monophosphate (cAMP) modulates a variety of cellular and physiologic functions in mammals, such as, cell division, endocrine function, and the immune response. Several therapeutically beneficial effects arise from elevations in cAMP. For example, cAMP mediates airway smooth muscle relaxation, so a rise in the levels of cAMP should result in bronchodilation. Second, increased intracellular concentrations of cAMP in inflammatory cells prevents their activation thus reducing inflammation. Therefore, compounds which modulate cAMP are useful in treating diseases such as asthma where both bronchoconstriction and inflammation are implicated.

The level of cAMP is controlled by a class of enzymes called phosphodiesterases which enzymatically deactivate cAMP. There are five general types of phosphodiesterases which are categorized according to their function and the type of cell from which they are isolated. For instance, high-affinity phosphodiesterase (PDE III) is isolated from human platelet cells and modulates platelet aggregation. Another type of phosphodiesterase (PDE IV) is found in various tissues but is the predominant form in human leukocytes; this enzyme modulates leukocyte activation and function associated with the immune response and inflammation. PDE IV is the principal isozyme in almost all human inflammatory cells. Both of these phosphodiesterases implement their control by modulating the cellular level of cAMP in their respective cells. Thus, inhibition of phosphodiesterases provides a method of modulating any cellular and bodily function that is controlled by cAMP.

Compounds that are nonspecific phosphodiesterase inhibitors are known, i.e., these compounds inhibit all or multiple types of phosphodiesterases. [See, Beavo, J. A. and D. H. Reifsyder, *Trends in Pharm. Science*, 11:150–155 (1990); and Nicholson, C. D., R. A. J. Challiss and M. Shahid, *Trends in Pharm. Science*, 12:19–27 (1991).] Since cAMP is involved in so many functions throughout the body, a nonspecific phosphodiesterase inhibitor has the potential to alter all of the functions modulated by cAMP. Thus, nonspecific phosphodiesterase inhibitors are of limited value because of numerous side-effects.

By contrast, selective PDE inhibitors have demonstrable clinical utility. Selective PDE IV inhibitors show smooth muscle relaxant activity in human tracheal and bronchial preparations in vitro. Selective PDE IV inhibitors block mediator synthesis and release in mast cells, basophils, monocytes and eosinophils, reduce respiratory burst, chemotaxis and degranulation in neutrophils and eosinophils, and suppress mitogen-induced lymphocyte proliferation. Thus, a selective PDE IV inhibitor can provide both symptomatic (bronchodilation) and prophylactic (antiinflammatory) benefit in asthma. The mixed PDE III/IV inhibitor, zardarverine, exhibits bronchodilatory activity in asthmatic subjects and the selective PDE IV inhibitor, tibneblast prevents spontaneous bronchoconstriction in asthmatic subjects. In view of the anti-inflammatory effects of selective PDE IV inhibitors, such inhibitors find particular utility in the treatment of diseases such as asthma where both bronchoconstriction and inflammation occur.

It has been surprisingly discovered that certain derivatives of 8-phenyl-1,6-naphthyridin-5-ones are potent selective inhibitors of Phosphodiesterase Type IV (PDE IV) enzyme. These compounds are well suited for use as a treatment for any disorder in which PDE IV function plays a role, such as where leukocyte activation or function is involved. In particular, these compounds are especially well suited for use as anti-inflammatory agents, immunosuppressive agents, anti-allograft rejection agents, anti-graft-vs-host disease agents, anti-allergic agents (e.g., asthma, rhinitis and atopic dermatitis), bronchodilation agents, anti-autoimmune disease agents or analgetic agents.

SUMMARY OF THE INVENTION

One aspect of the present invention relates to derivatives of 8-aryl-1,6-naphthyridin-5-ones, i.e., a compound of Formula I:

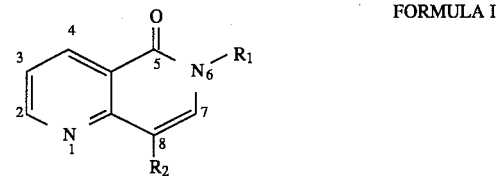

FORMULA I wherein:

$R_1$ is hydrogen, alkyl, lower-alkyl, cycloalkyl, heteroalkyl, heterocycloalkyl, aryl, heteroaryl, cycloalkyl lower-alkyl, heterocycloalkyl lower-alkyl, aralkyl or heteroaralkyl; and $R_2$ is aryl;

or a pharmaceutically acceptable salt or N-oxide thereof.

A preferred aspect of the invention is a compound of Formula I wherein:

$R_1$ is hydrogen, alkyl, lower-alkyl, cycloalkyl, heteroalkyl, heterocycloalkyl, aryl, heteroaryl, cycloalkyl lower-alkyl, heterocycloalkyl lower-alkyl, aralkyl or heteroaralkyl; and $R_2$ is optionally substituted phenyl; or a pharmaceutically acceptable salt or N-oxide thereof.

In another aspect, the invention relates to a pharmaceutical composition containing a therapeutically effective amount of a compound of Formula I admixed with at least one pharmaceutically acceptable excipient.

In still another aspect, the invention relates to a method of use of a compound of Formula I as an anti-inflammatory agent, immunosuppressive agent, anti-allograft rejection agent, anti-graft-vs-host disease agent, anti-allergic agent (e.g., asthma, rhinitis and atopic dermatitis), bronchodilation agents, anti-autoimmune disease agent or analgetic agent, by administering to a mammal in need of such treatment a therapeutically effective amount of a compound of Formula I or a pharmaceutically acceptable N-oxide or salt thereof.

Yet another aspect of the invention relates to the treatment of the above conditions or diseases by the selective inhibition of PDE IV.

In another aspect, this invention provides compositions useful in the treatment of inflammatory, allograft rejection, graft-vs-host disease, allergy, asthma, autoimmune or analgetic conditions or diseases in mammals comprising a therapeutically effective amount of a compound of Formula I and a pharmaceutically acceptable excipient.

DETAILED DESCRIPTION OF THE INVENTION

DEFINITIONS AND GENERAL PARAMETERS

The following definitions are set forth to illustrate and define the meaning and scope of the various terms used to describe the invention herein.

The term "alkyl" refers to a branched or straight chain acyclic, monovalent saturated hydrocarbon radical of one to twenty carbon atoms.

The term "heteroalkyl" refers to a branched or straight chain acyclic, monovalent saturated radical of two to twenty atoms in which at least one of the atoms in the chain is a heteroatom, such as, for example, nitrogen, oxygen or sulfur.

The term "lower-alkyl" refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "cycloalkyl" refers to a monovalent saturated carbocyclic radical of three to twelve carbon atoms, which can optionally be mono-, di-, or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl.

The term "heterocycloalkyl" refers to a monovalent saturated cyclic radical of one to twelve atoms, having at least one heteroatom (such as nitrogen, oxygen or sulfur) within the ring, said radical being optionally mono-, di-, or trisubstituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Further, the term also includes instances where an atom of a heterocycle has been oxidized, e.g., N-oxides, sulfoxides and sulfones. Examples of heterocyloalkyl radicals include piperidinyl, piperazinyl, pyrrolidinyl, pyrrolodinonyl, tetrahydrofuranyl, morpholinyl and tetrahydrothiophenyl.

The term "alkylene" refers to a fully saturated, acyclic, divalent, branched or straight chain hydrocarbon radical of one to twenty carbon atoms. This term is further exemplified by radicals such as methylene, ethylene, n-propylene, ethylethylene, and n-heptylene.

The term "lower-alkylene" refers to a fully saturated, acyclic, divalent, branched or straight chain hydrocarbon radical of one to six carbon atoms. This term is further exemplified by such radicals as methylene, ethylene, n-propylene, i-propylene, n-butylene, i-butylene (or 2-methylpropylene), isoamylene (or 3,3 dimethylpropylene), pentylene, and n-hexylene.

The term "cycloalkyl lower-alkyl" refers to a cycloalkyl group appended to a lower-alkyl radical. This term is exemplified by, but not limited to, groups such as cyclopropylmethyl, cyclopentylmethyl, cyclopentylethyl, and cyclopentylpropyl.

The term "heterocycloalkyl lower-alkyl" refers to a heterocycloalkyl group appended to a lower-alkyl radical. This term is exemplified by, but not limited to, groups such as 2-furylmethyl, 3-furylmethyl, piperidinoethyl, 2-piperidylmethyl, 2-morpholinylmethyl, and morpholinomethyl.

The term "optionally substituted phenyl" refers to a phenyl group which can optionally be mono-, di-, or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Alternatively, two adjacent positions of the phenyl group may be substituted with a methylenedioxy or ethylenedioxy group.

The term "aryl" refers to an aromatic monovalent carbocyclic radical having a single ring (e.g., phenyl) or two condensed rings (e.g., naphthyl), which can optionally be mono-, di-, or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. Alternatively, two adjacent positions of the aromatic ring may be substituted with a methylenedioxy or ethylenedioxy group.

The term "aralkyl" refers to an aryl group appended to a lower-alkyl radical. This term is exemplified by, but not limited to, groups such as benzyl, 2-phenylethyl and 2-(2-naphthylethyl).

The term "heteroaryl" refers to aromatic monovalent mono-or poly-cyclic radical having at least one heteroatom within the ring, e.g., nitrogen, oxygen or sulfur, wherein the aromatic ring can optionally be mono-, di- or tri-substituted, independently, with alkyl, lower- alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. For example, typical heteroaryl groups with one or more nitrogen atoms are tetrazoyl, pyridyl (e.g., 4-pyridyl, 3-pyridyl, 2-pyridyl), pyridazinyl, quinolyl (e.g. 2-quinolyl, 3-quinolyl etc.), imidazolyl, isoquinolyl, pyrazolyl, pyrazinyl, pyrimidinyl, pyridonyl or pyridazinonyl; typical oxygen heteroaryl radicals with an oxygen atom are 2-furyl, 3-furyl or benzofuranyl; typical sulfur heteroaryl radicals are thienyl, and benzothienyl; typical mixed heteroatom heteroaryl radicals are furazanyl and phenothiazinyl. Further the term also includes instances where a heteroatom within the ring has been oxidized, such as, for example, to form an N-oxide or sulfone.

The term "heteroaralkyl" refers to a heteroaryl group appended to a lower-alkyl radical. This term is exemplified by, but not limited to, groups such as pyridylmethyl (e.g., 4-pyridylmethyl, 3-pyridylmethyl and 2-pyridylmethyl), pyridylethyl, pyridylpropyl, pyridylbutyl, quinolylmethyl, furylmethyl, and thienylmethyl.

The term "lower-alkoxy" refers to the group —O—R where R is lower-alkyl.

The term "methylene" refers to the group —CH$_2$—.

The term "methylenedioxy" refers to the group —O—CH$_2$—O—.

The term "ethylenedioxy" refers to the group —O—CH$_2$—CH$_2$—O—.

The term "carbonyl" refers to the group —C(O)—.

The term "hydroxycarbonyl" refers to the group —C(O)OH.

The term "lower-alkoxycarbonyl" refers to the group —C(O) OR where R is lower-alkyl.

The term "acyl" refers to the group —C(O)—R, where R is lower-alkyl, e.g., methylcarbonyl (acetyl) and ethylcarbonyl (propionyl or propanoyl).

The term "carbmoyl" refers to the group —C(O)NR'R where R and R' are independently hydrogen or lower-alkyl, e.g., where R is hydrogen and R' is lower-alkyl the group is mono- lower-alkylcarbamoyl, where R and R' are lower-alkyl the group is di-lower-alkylcarbamoyl.

The term "halo" refers to fluoro, bromo, chloro and iodo.

The term "lower-alkylthio" refers to the group R—S—, where R is lower-alkyl.

The term "lower-alkylsulfinyl" refers to the group R—S(O)—, where R is lower-alkyl.

The term "lower-alkylsulfonyl" refers to the group R—S(O)$_2$—, where R is lower-alkyl.

The term "lower-alkoxysulfonyl" refers to the group RO—S(O)$_2$—, where R is lower-alkyl.

The term "hydroxysulfonyl" refers to the group HO—S(O$_2$)—.

The term "aryloxy" refers to the group R—O— where R is an aryl group, such as for example phenoxy.

The term "arylamino" refers to the group R—NH— where R is an aryl group, such as for example, phenylamino.

The term "diarylamino" refers to the group R(R')—N— where R and R' are aryl groups such as for example, diphenylamino.

The term "tetrazolyl" refers to the group

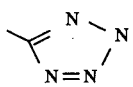

The term "electron withdrawing group" refers to a radical group that has a greater affinity for electrons than a hydrogen atom would if it occupied the same position in the molecule. For example, typical electron withdrawing groups are halo (e.g., chloro, bromo, iodo and fluoro), nitro, trifluoromethyl, cyano, hydroxycarbonyl, methoxycarbonyl and methylcarbonyl.

The term "leaving group" means a group capable of being displaced by a nucleophile in a chemical reaction, for example halo, alkyl sulfonates (e.g., methanesulfonate), aryl sulfonates, phosphates, sulfonic acid, sulfonic acid salts, and the like.

The term "alkylating agent" refers to a chemical compound such as R-X, where X is a leaving group such that the compound is capable of reacting with a nucleophile (Nu), such as, for example, N$^6$ of compounds such as Formula I, resulting in the attachment of the R group to the nucleophile.

A "pharmaceutically acceptable salt" may be any salt derived from an inorganic or organic acid or base. Salts may be derived from acids or bases.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like.

The base addition salts are derived from inorganic bases such as sodium hydroxide, potassium hydroxide, lithium hydroxide, ammonia, calcium hydroxide, magnesium hydroxide and the like. Cations derived from organic bases include those formed from primary, secondary and tertiary amines, such as isopropylamine, diethylamine, trimethylamine, triethylamine, pyridine, cyclohexylamine, ethylene diamine, monoethanolamine, diethanolamine, triethanolamine, and the like.

As used herein, the term "allograft rejection" refers to the humoral or cellular immune response mounted by the immune system of a mammal after it has received a histo-incompatible tissue graft from another mammal of the same species, thereby producing tissue injury to the graft in such a recipient.

As used herein, the term "graft-vs-host disease" refers to the immune response that originates from transplanted graft tissue, for example, transplanted bone-marrow tissue, and that is directed towards the host tissue, thereby producing tissue injury in the host.

As used herein, the term "autoimmune disease" refers to disorders wherein the immune system of a mammal mounts a humoral or cellular immune response to the mammal's own tissue or to antigenic agents that are not intrinsically harmful to the mammal, thereby producing tissue injury in such a mammal. Examples of such disorders include, but are not limited to, systemic lupus erythematosus, rheumatoid arthritis and type I diabetes.

As used herein, the terms "treatment" or "treating" of a condition and/or a disease in a mammal, means:

(i) preventing the condition or disease, that is, avoiding any clinical symptoms of the disease;

(ii) inhibiting the condition or disease, that is, arresting the development or progression of clinical symptoms; and/or (iii) relieving the condition or disease, that is, causing the regression of clinical symptoms. The conditions and diseases treated in the present invention include, inflammation, pain, pyrexia, autoimmune disease, allograft rejection, graftors-host disease, allergies, asthma and uveitis.

As used herein, the term "therapeutically effective amount" refers to that amount of a compound of Formula I which, when administered to a mammal in need thereof, is sufficient to effect treatment (as defined above) as an anti-inflammatory agent, immunosuppressive agent, anti-allograft rejection agent, anti-graft-vs-host disease agent, anti-allergy agent, anti-asthmatic agent, anti-autoimmune disease agent or analgetic agent. The amount that constitutes a "therapeutically effective amount" will vary depending on the compound, the condition or disease and its severity, and the mammal to be treated, its weight, age, etc., but may be determined routinely by one of ordinary skill in the art with regard to contemporary knowledge and to this disclosure.

As used herein, the term "q.s." means adding a quantity sufficient to achieve a stated function, e.g., to bring a solution to a desired volume (e.g., 100 mL).

As used herein, the term "mp" refers to melting point. All temperatures are given in degrees Celsius (i.e., °C).

Unless specified to the contrary, the ranges of time and temperature described herein are approximate, e.g., "from 8 to 24 hours at from 10° C. to 100° C." means from about 8 to about 24 hours at about 10° C. to about 100° C.

The term "inert" in inert atmosphere refers to an atmosphere substantially free of oxygen and moisture, such as, for example, anhydrous nitrogen or argon.

Isolation and purification of the compounds and intermediates described herein can be effected, if desired, by any suitable separation or purification procedure such as, for example, filtration, extraction, crystallization, column chromatography, preparative high pressure liquid chromatography (preparative HPLC), thin-layer chromatography or thick-layer chromatography, or a combination of these procedures, referred to hereinafter as "conventional means". Specific illustrations of suitable separation and isolation procedures can be had by reference to the examples hereinbelow. However, other equivalent separation or isolation procedures can also be used.

The following numbering and nomenclature system will be used for naming the compounds of the invention.

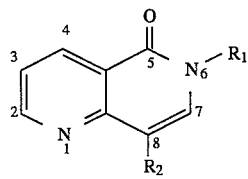

The compound of Formula I where $R_1$ is hydrogen and $R_2$ is 3-chlorophenyl can be named 8-(3-chlorophenyl)-1,6, naphthyridin-5-One.

The compound of Formula I where $R_1$ is benzyl and $R_2$ is 3-chlorophenyl can be named 6-benzyl-8-(3-chlorophenyl)-1,6-naphthyridin-5-one.

SYNTHESIS OF COMPOUNDS OF THE INVENTION

The starting materials and reagents used in preparing the compounds of this invention depicted in reaction Schemes A-D are either available from commercial suppliers such as Aldrich Chemical Co. or are prepared by methods known to those skilled in the art following procedures set forth in references such as, "Fieser and Fieser's Reagents for Organic Synthesis", Volumes 1–15, John Wiley and Sons, 1991; "Rodd's Chemistry of Carbon Compounds", Volumes 1–5 and Supplementals, Elsevier Science Publishers, 1989; and "Organic Reactions", Volumes 1–40, John Wiley and Sons, 1991.

I Preparation of Compounds of Formula I where $R_1$ is Hydrogen

The following Reaction Scheme A represents an example of the synthesis of Compounds of Formula I where $R_1$ is hydrogen. A 2,3-pyridinedicarboxylic anhydride is condensed with an aryl organometallic reagent to give a 2-aroyl-3-methylnicotinate of Formula 3 which is subsequently reduced to an arylmethyl nicotinic acid of Formula 4. Formylation of 4 followed by cyclization gives a pyrano[3,4-b]pyridinone of Formula 5 which is condensed with an ammonium salt to give an 8-aryl-6-naphthyridin-5-one of Formula I (where $R_1$ is not hydrogen).

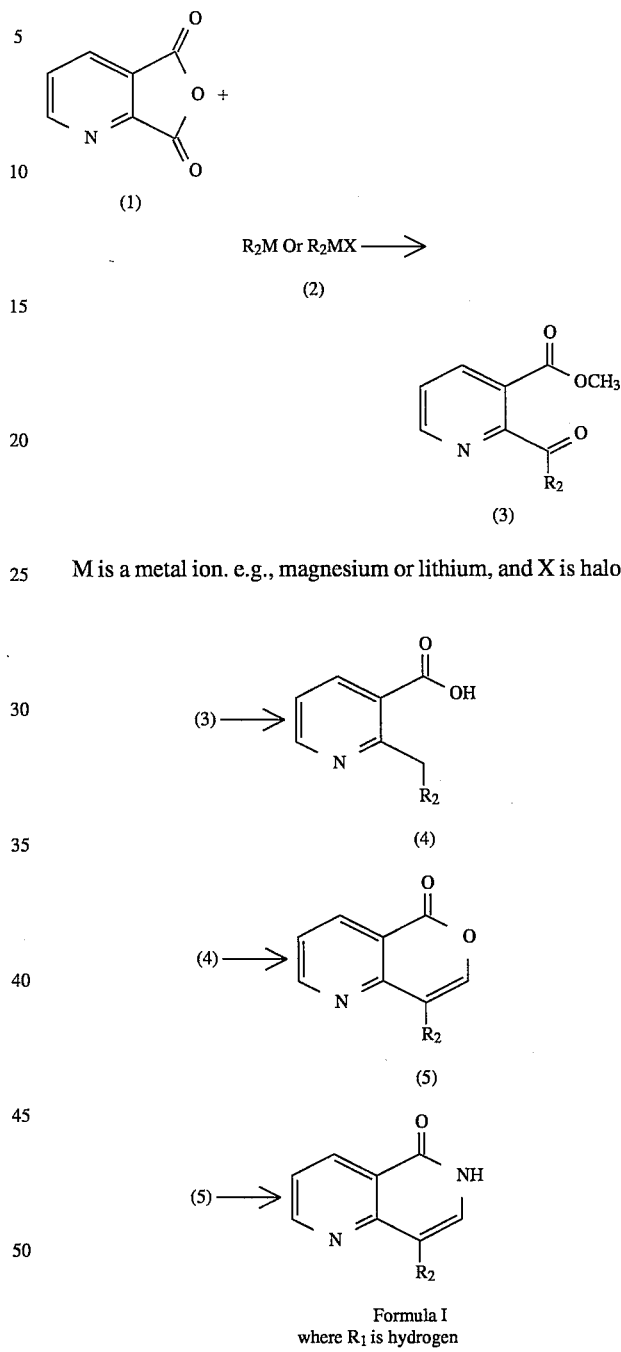

M is a metal ion. e.g., magnesium or lithium, and X is halo

Preparation of Compounds of Formula 3

The starting material, a 2,3-pyridinedicarboxylic anhydride is dissolved in a anhydrous aprotic solvent, such as, for example, an ether such as tetrahydrofuran, dioxane, dimethoxyethane, or an aromatic hydrocarbon such as benzene or toluene under an inert atmosphere and cooled to a temperature between about 0° to −100° C., preferably about −60° to −80° C., more preferably about −78° C. To this is slowly added about 1 to 2 molar equivalents, preferably about 1 molar equivalent of an aryl organometallic reagent such, as for example, an aryl organomagnesium or organolithium reagent, preferably phenyl magnesium bromide or chlorophenyl magnesium bromide in a suitable inert solvent such as, for example, tetrahydrofuran or toluene. After about 1 to 5 hours at this temperature, preferably about 1 to 3 hours, more preferably about 2 hours, the reaction is allowed to warm to a temperature of about 20° to 30° C., preferably to ambient temperature within this range and stirred at the above temperature for about 6 to 72 hours, preferably 12 to 24 hours. The reaction is then heated at a temperature of about 50 to 100° C., preferably at about 60° to 80° C., more preferably at about 65° C. The reaction is cooled to about 20° to 30° C., preferably about ambient temperature, acidified with, for example, hydrochloric acid, and the organic layer is separated. The organic layer is concentrated and resuspended in a acidic alcoholic medium, preferably an acidic lower alkyl alcohol, more preferably an acidic methanolic medium, and heated at about 40°–100° C., preferably about 60° to 80° C., more preferably about 65° C., for about 12 to 24 hours, preferably about 18 hours. The reaction product, a compound of Formula 3 is isolated and purified by conventional means.

Preparation of Compounds of Formula 4

The compound of Formula 3 obtained above is reduced to the corresponding 2-arylmethylnicotinic acids of Formula 4 by techniques such as dissolving metal reductions, preferably using zinc or mercury, or electrophilic metal hydride reductions using reagents such as, for example, $AlH_3$. For example, a compound of Formula 3 is suspended in a basic aqueous medium, preferably an ammoniacal medium to which is gradually added a catalytic amount of a copper salt, preferably copper(II) sulfate, and 5 to 20 molar equivalents, preferably about 8 to 12 molar equivalents, more preferably 10 molar equivalents of a zinc-mercury amalgam or zinc powder, preferably zinc powder. The mixture is heated at about 90° to 100° C., preferably at reflux, for about 5 to 10 days, preferably about 5 to 7 days, more preferably about 6 days. The mixture is cooled, filtered and acidified. The reaction product, a 2-arylmethyl nicotinic acid of Formula 4 is isolated and purified by conventional means.

Preparation of Compounds of Formula 5

A 2-arylmethyl nicotinic acid of Formula 4 is condensed with reagents such as orthoesters, alkoxyacetals or aminoacetals to give an 8-substituted pyrano[3,4-b]pyridine-5-one of Formula 5. A compound of Formula 4 is dissolved in a polar anhydrous solvent, preferably dimethyl formamide and treated with about 1 to 5 molar equivalents, preferably 2 to 3 molar equivalents of, for example, dimethyl formamide acetal. The reaction mixture is heated at about 60°–100° C., preferably at about 70°–90° C., more preferably about 80° C, for about 1 to 24 hours, preferably about 2 to 15 hours, more preferably about 10 hours. The reaction mixture is cooled to ambient temperature and an 8-substituted pyrano [3,4-b]pyridin-5-one of Formula 5 is isolated and purified by conventional means, preferably column chromatography.

Preparation of Compounds of Formula I when $R_1$ is Hydrogen

A solution of an 8-substituted pyrano[3,4-b]pyridin-5-one of Formula 5 in a dipolar aprotic solvent such as N-methyl pyrrolidinone, dimethyl sulfoxide or dimethyl formamide, preferably dimethyl formamide, is combined with about 1 to 3 molar equivalents, preferably about 1 to 2 molar equivalents, more preferably 1.5 molar equivalents, of an ammonium salt such as, for example, ammonium acetate and heated at about 40°–100° C., preferably at 50°–80° C., more preferably 60°–70° C. for about 0.5 to 24 hours, preferably about 1 to 18 hours, more preferably about 2 to 15 hours. The reaction product, an 8-aryl-1,6-naphthyridin-5-one of Formula I where $R_1$ is hydrogen is isolated and purified by conventional means.

II. Preparation of Compounds of Formula I when $R_1$ is not Hydrogen

A. From Compounds of Formula 5

The following Reaction Scheme B represents an example of a synthesis of a compound of Formula I where $R_1$ is not hydrogen by condensing a pyrano[3,4-b]pyridin-5-one compound of Formula 5 with an primary amine.

REACTION SCHEME B

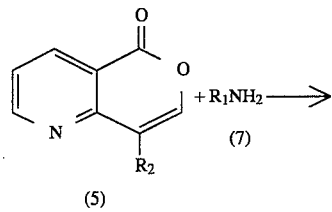

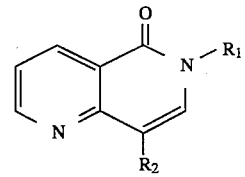

Formula I

As shown in Reaction Scheme B, a solution of an 8-substituted pyranopyridin-5-one of Formula 5 in a dipolar aprotic solvent such as N-methyl pyrrolidinone, dimethyl sulfoxide or dimethyl formamide, preferably dimethyl formamide, is combined with about 1–2 molar equivalents, preferably about 1–1.5 molar equivalents, more preferably about 1.2 equivalents of a primary amine, such as, for example, an aliphatic, alkyl, cycloalkyl, aromatic, aralkyl or heteroaralkyl primary amine and heated under an inert atmosphere at about 50°–100° C., preferably about 60°–90° C., preferably about 80° C, for about 12–48 hours, preferably about 12–24 hours, more preferably about 15 hours. The reaction product, a 6,8-substituted-1,6-naphthyridin-5-one of Formula I is isolated and purified by conventional means.

B. From Compounds of Formula I where R is Hydrogen

The following Reaction Schemes C and D represent examples of syntheses of compounds of Formula I where $R_1$ is not hydrogen by alkylating $N^6$ of compounds of Formula I where $R_1$ is hydrogen.

REACTION SCHEME C

where $R_1$ is hydrogen (6)

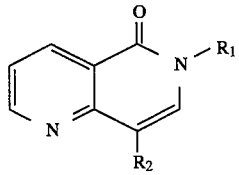

Formula I

11

REACTION SCHEME D

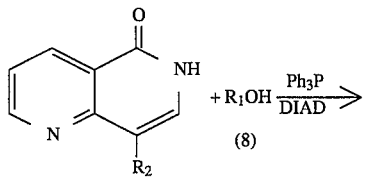

Formula I
where $R_1$ is hydrogen

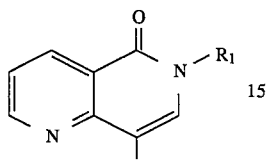

Formula I

As shown in Reaction Scheme C, a 6-unsubstituted, 8-substituted- 1,6-naphthyridin-5-one of Formula I is treated with a suitable alkylating agent such as an alkyl halide, mesylate or tosylate, usually in the presence of a tertiary organic base such as, for example, triethylamine, or an inorganic base such as, for example, potassium carbonate. Alternatively, alkylating agents containing cycloalkyl, heteroalkyl, heterocycloalkyl, aromatic, aryl, heteroaryl, aralkyl or heteroaralkyl groups can be used. A suspension of a 6-unsubstituted, 8-substituted-1,6-naphthyridin- 5-one of Formula I and about 1 to 5 molar equivalents, preferably about 2 to 5 molar equivalents, more preferably about 3 molar equivalents of potassium carbonate in a dipolar aprotic solvent such as N-methyl pyrrolidinone, dimethyl sulfoxide or dimethyl formamide, preferably dimethyl formamide, is treated gradually with about 1 to 3 molar equivalents, preferably 1 to 2 molar equivalents, more preferably about 1.5 to 2 molar equivalents, of an alkyl, cycloalkyl, heteroalkyl, heterocycloalkyl, aromatic, aryl, heteroaryl, aralkyl or heteroaralkyl halide, such as, for example, iodoethane, benzyl bromide or picolyl chloride under an inert atmosphere. The mixture is allowed to react at about 15°–80° C., preferably about 20°–50° C., more preferably at ambient temperature. The reaction mixture is poured into water and a 6,8-substituted-1,6-naphthyridin-5-one of Formula I is isolated and purified by conventional means, preferably by crystallization.

Alternatively, as shown in Reaction Scheme D, a 6-unsubstituted, 8-substituted-1,6-naphthyridin-5-one of Formula I is treated with a mixture of an alcohol, triphenylphosphine and a dialkylazodicarboxylate to give a 6-substituted compound of Formula I. The alcohol can be an alkyl, cycloalkyl, heteroalkyl, heterocycloalkyl, aralkyl, or heteroaralkyl alcohol. A mixture of a 6-unsubstituted, 8-aryl-1,6-naphthyridin- 5-one of Formula I, about 1 to 1.5 molar equivalents, preferably about 1 to 1.3 molar equivalents, more preferably 1.2 molar equivalents of an alcohol and about 1 to 2 molar equivalents, preferably about 1 to 1.5 molar equivalents, more preferably about 1.5 molar equivalents of 55triphenylphosphine is suspended in a polar solvent such as tetrahydrofuran, dimethoxy ethane or diethyl ether. The suspension is treated gradually with about 1 to 2 molar equivalents, preferably about 1 to 1.5 molar equivalents, more preferably about 1.5 molar equivalents of diisopropylazodicarboxylate(DIAD). The reaction product, a 6,8-substituted- 1,6-naphthyridin-5-one of Formula I, is isolated a purified by conventional means, preferably by chromatography and crystallization.

12

Following the procedures outlined above are obtained compounds of Formula I as listed in Table I below.

TABLE I

| $R_1$ | $R_2$ |
|---|---|
| Ethyl | Phenyl |
| Benzyl | Phenyl |
| 4-Pyridylmethyl | Phenyl |
| H | 3-Chlorophenyl |
| Isopropyl | " |
| Ethyl | " |
| cyclopropylmethyl | " |
| cyclopentylmethyl | " |
| benzyl | " |
| 4-pyridylmethyl | " |
| 2-furylmethyl | " |
| 2-thienylmethyl | " |
| cyclopropylmethyl | 3,4-dichlorophenyl |
| 2-furylmethyl | 3,4-dichlorophenyl |
| cyclopropylmethyl | 3,4-methylenedioxyphenyl |
| 2-furylmethyl | 3,4-methylenedioxyphenyl |
| cyclopropylmethyl | 3,4-ethylenedioxyphenyl |
| 2-furylmethyl | 3,4-ethylenedioxyphenyl |
| cyclopropylmethyl | 3-nitrophenyl |
| 2-furylmethyl | 3-nitrophenyl |
| cyclopropylmethyl | 3-trifluorophenyl |
| 2-furylmethyl | 3-trifluorophenyl |
| cyclopropylmethyl | 3-methoxyphenyl |
| 2-furylmethyl | 3-methoxyphenyl |
| cyclopropylmethyl | 3-cyanophenyl |
| 2-furylmethyl | 3-cyanophenyl |

PREFERRED COMPOUNDS

Presently preferred are the compounds of Formula I where $R_2$ is optionally substituted phenyl.

Especially preferred are compounds of Formula I where $R_2$ is phenyl substituted at the 3-position with an electron withdrawing group.

Also especially preferred are the compounds of Formula I where $R_2$ is 3-chlorophenyl.

Of the compounds of Formula I wherein $R_2$ is 3-chlorophenyl, especially preferred are those where $R_1$ is benzyl, furylmethyl, thienylmethyl, cyclopropylmethyl and cyclopentylmethyl.

PREFERRED PROCESSES AND LAST STEPS

A preferred process for making 6,8-substituted-1,6-naphthyridin- 5-ones involves combining an 8-substituted pyrano [3,4-b]pyridin-5-one with a primary amine. Another preferred process for making 6,8-substituted-1,6-naphthyridin-5-ones involves combining the corresponding 6-Unsubstituted 8-substituted- 1,6-naphthyridin-5-one (compounds of Formula I where $R_1$ is hydrogen) with an alkylating agent and a suitable base. A particularly preferred process for making 6,8-substituted-1,6-naphthyridin- 5-ones involves combining the corresponding 6-unsubstituted 8-substituted-1,6-naphthyridin-5-one (compounds of Formula I where $R_1$ is hydrogen) with an alcohol, triphenylphosphine and diisopropylazodicarboxylate.

UTILITY, TESTING AND ADMINISTRATION

GENERAL UTILITY

The compounds of this invention, including the pharmaceutically acceptable N-oxides and salts thereof, and the compositions containing them are particularly useful as anti-inflammatory, immunosuppressive, anti-allograft rejection, anti-graft-vs-host disease, anti-allergic agents (e.g., asthma, rhinitis and atopic dermatitis), bronchodilation agents, anti-autoimmune disease or analgetic agents. The compounds of this invention act as selective PDE IV inhibitors, thereby modulating cAMP levels. Thus, these compounds are of use for the treatment of cAMP related conditions or diseases, particularly those that are modulated by leukocyte cAMP, and asthma.

For example, inflammation, autoimmune diseases, grafts-host disease and allograft rejection are conditions that are manifested by the proliferation of lymphocytes. The proliferation is triggered by the presence of cAMP at specific levels. Inhibition of lymphocyte proliferation is accomplished by increasing levels of cAMP resulting from the inhibition of lymphocyte phosphodiesterase.

TESTING

Potency and selectivity of compounds as inhibitors of PDE IV is determined by following, for example, the procedures described in Example 9, or modifications thereof.

The immunomodulatory and anti-inflammatory activity of the compounds of the invention can be determined by a variety of assays utilizing both in vitro and in vivo procedures.

Inhibition of the proliferation of lymphocytes in response to mitogenic stimulation is determined by the procedures described by Greaves, et al. ["Activation of human T and B lymphocytes by polyclonal mitogens," *Nature*, 248, 698–701 (1974)], or modifications thereof (see, Example 10).

Inhibition of lymphocyte activation in response to antigenic challenge is determined in vitro by inhibition of a cytolytic T-cell assay (CTL) as described by Wunderlich, et al., *Nature* (1970), Vol. 228, p. 62, or a modification thereof.

Immune modulation is determined by in vivo procedures utilizing the Jerne Hemolytic Plaque Assay, [Jerne, et al., "The agar plaque technique for recognizing antibody producing cells," *Cell-bound Antibodies*, Amos, B. and Kaprowski, H. editors (Wistar Institute Press, Philadelphia) 1963, p. 109] or a modification thereof (see, Example 11).

Anti-inflammatory activity is determined by the Arachidonic Acid-Induced Mouse Ear Edema Assay [Young, et al., *J. Invest. Derm.*, 82:367–371 (1984)] (see, Example 12).

Anti-inflammatory activity is also determined by the Adjuvant Arthritis assay [Pearson, C. M., *Proc. Soc. Exp. Biol. Med.*, 91:95–101 (1956)], or modifications thereof (see Example 13).

Anti-autoimmune activity in treating autoimmune disease can be determined utilizing the survivability of MRL/lpr mice described by Theofilopoulos, et al., *Advances in Immunology*, Vol 37, pages 269–390 (1985) on pages 274–276, or a modification thereof (see Example 14).

Analgetic activity is determined by the Phenylquinone-induced Mouse Writhing Assay [Hendershot, et al., *J. Pharmacol. Exp. Ther.*, 125:237–240 (1959)] (see Example 15).

Anti-allergenic activity and anti-asthmatic activity is determined by measuring the inhibition of antigen-induced bronchoconstriction and total cellular infiltration and eosinophil influx into the airway lumen of antigen-sensitized guinea pigs as described by Hutson et al., *American Review of Respiratory Disease*, Early and Late-Phase Bronchoconstriction after Allergen Challenge of Nonanesthetized Guinea Pigs, 137, 548–557 (1988), or modifications thereof (see Example 16).

ADMINISTRATION

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (%w) to about 99.99% w of the drug based on the total formulation and about 0.01% w to 99.99% w excipient. Preferably the drug is present at a level of about 10% w to about 70% w.

Generally, an acceptable daily dose is of about 0.001 to 50 mg per kilogram body weight of the recipient per day, preferably about 0.05 to 25 mg per kilogram body weight per day, and most preferably about 0.01 to 10 mg per kilogram body weight per day. Thus, for administration to a 70 kg person, the dosage range would be about 0.07 mg to 3.5 g per day, preferably about 3.5 mg to 1.75 g per day, and most preferably about 0.7 mg to 0.7 g per day depending upon the individuals and disease state being treated. Such use optimization is well within the ambit of those of ordinary skill in the art.

Administration can be via any accepted systemic or local route, for example, via parenteral, oral (particularly for infant formulations), intravenous, nasal, bronchial inhalation (i.e., aerosol formulation), transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula I and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula I. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

INTRAVENOUS ADMINISTRATION

Intravenous injection has proven to be an important route of administration for therapeutic agents. The compounds of the present invention can be administered via this route, for example, by dissolving the compound, salt or N-oxide thereof in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

ORAL ADMINISTRATION

Oral administration can be used to deliver the compound of Formula I using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the compound of Formula I, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

AEROSOL ADMINISTRATION

Aerosol administration is an effective means for delivering a therapeutic agent directly to the respiratory tract. Some of the advantages of this method are: 1) it circumvents the effects of enzymatic degradation, poor absorption from the gastrointestinal tract, or loss of the therapeutic agent due to the hepatic first-pass effect; 2) it administers therapeutic agents which would otherwise fail to reach their target sites in the respiratory tract due to their molecular size, charge or affinity to extra-pulmonary sites; 3) it provides for fast absorption into the body via the alveoli of the lungs; and 4) it avoids exposing other organ systems to the therapeutic agent, which is important where exposure might cause undesirable side effects. For these reasons, aerosol administration is particularly advantageous for treatment of asthma, local infections of the lung, and other diseases or disease conditions of the lung and respiratory tract.

There are three types of pharmaceutical inhalation devices, nebulizers inhalers, metered-dose inhalers (MDI) and dry powder inhalers (DPI). Nebulizer devices produce a stream of high velocity air that causes the therapeutic agent (which has been formulated in a liquid form) to spray as a mist which is carried into the patient's respiratory tract. MDIs typically have the formulation packaged with a compressed gas. Upon actuation, the device discharges a measured amount of therapeutic agent by compressed gas, thus affording a reliable method of administering a set amount of agent. Historically, MDIs have used chlorofluorocarbons (CFC) as the compressed gas to propel the therapeutic agent. In recent years, CFCs have been linked with the depletion of the earth's ozone layer. As a result of this, alternative propellants that are non-ozone threatening are being sought out as potential replacements for CFCs.

DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation. Examples of DPI's being used are Spinhaler® (for the administration of disodium cromoglycate), Rotahaler® (for albuterol) and Turbuhaler® (for terbutaline sulfate). All of the above methods can be used for administering the present invention, particularly for the treatment of asthma and other similar or related respiratory tract disorders.

LIPOSOMAL FORMULATIONS

Pharmaceutical formulations based on liposomes have recently reached human clinical trials. Their benefits are believed to be related to favorable changes in tissue distribution and pharmacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151:704–710 (1985); Gotfredsen et al., *Biochemical Pharmacology*, 32:3389–3396 (1983)]; or to the reticuloendothelial system [see Eppstein et al., *Int. J. Immunotherapy*, 2:115–126 (1986)], to increase duration of drug action [see: Gabizon et al., *Cancer Res.*, 42:4734 (1982); Eppstein et al., *Delivery Systems for Peptide Drugs*, Eds. S. S. Davis, L. Illum and E. Tomlinson, Plenum Pub. Corp., New York, pp. 277–283; C. A. Hunt, *Biochemica et Biophysica Acta.*, 719: 450–463 (1982); and Senior et al., *Biochemica et Biophysica Acta.*, 839:1–8 (1985)], or to divert a drug away from organs that are particularly sensitive to its toxic effects [see: Weinstein et al., *Pharmac. Ther.*, 24:207–233 (1983); Olson et al., *Eur. J. Cancer Clin. Oncol.*, 18:167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing are incorporated herein by reference.

SUPPOSITORIES

For systemic administration via suppository, traditional binders and carriers include, for example, polyethylene glycols or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

LIQUIDS

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pennsylvania, 16th Ed., 1980. The composition to be administered will, in any event, contain a quantity of the active compound(s) in a pharmaceutically effective amount for relief of the particular condition being treated in accordance with the teachings of this invention.

EXAMPLES

The following examples are given to enable those skilled in the art to more clearly understand and to practice the present invention. They should not be considered as limiting the scope of the invention, but merely as being illustrative and representative thereof.

EXAMPLE 1

PREPARATION OF METHYL 2-BENZOYLNICOTINATES

A. Formula 3 where $R_2$ is phenyl

To a suspension of 29.84 grams 2,3-pyridinedicarboxylic anhydride in 300 ml THF under an atmosphere of dry nitrogen was added dropwise 200 ml of a 1.0M solution of phenyl magnesium bromide at −78° C. After two hours the reaction mixture was warmed to 21° C. and stirred overnight. The mixture was then refluxed for 24 hours, cooled, treated with 220 ml 1N HCl, stirred one hour, and transferred to separatory funnel. The THF layer was dried over magnesium sulfate, filtered and concentrated under vacuum to give 44.26 grams crude material which was then dissolved in 400 ml anhydrous methanol. To this solution was carefully added 10 ml conc. $H_2SO_4$. The solution was then refluxed overnight under an atmosphere of nitrogen. The mixture was cooled and concentrated under vacuum, neutralized with saturated sodium carbonate solution, and extracted with dichloromethane. The mixture was then dried over magnesium sulfate, filtered and concentrated under vacuum to give 42.71 grams crude material. The crude material was dissolved with a minimum amount of dichloromethane and treated by silica gel [column chromatography, eluted with ethyl acetate/hexane (1:3)] to give 12.35 grams (26% yield) of the desired methyl 2-benzoylnicotinate as a white powder. Characteristic analytical data are as follows: mp 74° C.; TLC in 1:3 EtOAc/Hex; $^1$H NMR (CDCl$_3$, 300 MHz) δ3.77 (s, 3H), 7.45–7.85 (m, 6H), 8.37 (dd, 1H, J=8.0, 1.6 Hz), 8.82 (dd, 1H, J=4.8, 1.5 Hz); mass spectrum (EI), m/e 421.

B. Formula 3 where $R_2$ is 3-chlorophenyl.

To a suspension of 29.84 grams 2,3-pyridinedicarboxylic anhydride [Aldrich] in 200 ml toluene under an atmosphere of dry nitrogen was added dropwise 200 ml of a 1.0M solution of freshly prepared 3-bromomagnesiochlorobenzene [4.86 grams magnesium turnings and 23.5 ml of 1-bromo-3-chlorobenzene in 200 ml THF] at −78° C. After two hours the reaction mixture was warmed to 21° C. and stirred overnight. The flask was then equipped with a condenser and the reaction was refluxed for 24 hours. The reaction mixture was cooled and then treated with 210 ml 1N HCl, stirred four hours and then transferred to separatory funnel. The THF/toluene layer dried over magnesium sulfate, filtered and concentrated under vacuum to give 39 grams crude material which was suspended in 500 ml methanol saturated with HCl and refluxed overnight. The reaction mixture was cooled, filtered and concentrated under vacuum to give 26.72 grams of crude material which was chromatographed eluting with 1:3 ethyl acetate/hexanes to give 9.85 grams (18% yield) of the desired 2-(3-chlorobenzoyl) methylnicotinate as a white powder. Characteristic analytical data are as follows: mp 62° C.; TLC in 1:3 EtOAc/Hex; $^1$H NMR (CDCl$_3$, 300 MHz) δ3.77 (s, 3 H), 7.34–7.80 (m, 5H), 8.33 (dd 1H J=8.0, 1.6 Hz), 8.78 (dd, 1H J=4.7, 1.6 Hz); mass spectrum (EI), m/e 275.

C. Compounds of Formula 3 Where $R_2$ is varied.

By following the procedures described in Part A of this Example and substituting for phenyl magnesium bromide with other aryl organometallic compounds $R_2MgX$ or $R_2Li$ there are obtained the corresponding substituted methyl 2-benzoylnicotinates compound of Formula 3 wherein $R_2$ is any one of the groups listed below in Table II.

TABLE II $R_2$ 3-chlorophenyl
4-ochlorophenyl
3,4-dichlorophenyl
3,4-methylenedioxyphenyl
3,4-ethylenedioxyphenyl
3-nitrophenyl
3-methoxyphenyl
3-trifluoromethylphenyl
3-cyanophenyl
3-methylthiophenyl

EXAMPLE 2

PREPARATION OF 2-BENZYLNICOTINIC ACIDS

A. Formula 4 where $R_2$ is phenyl

Methyl 2-Benzoylnicotinate (2.41 g., 10 mmoles) was dissolved in 250 ml ammonium hydroxide. To this solution was carefully added a catalytic amount of copper (II) sulfate (approx. 100 mg) and zinc powder (7.0 g., 100 mmoles). The mixture was refluxed for 6 days and allowed to cool. The mixture was filtered (pad of celite), acidified to pH 5 with 1N HCl, exhaustively extracted with ethyl acetate, washed with brine, dried over sodium sulfate, filtered, concentrated under vacuum, and purified by column chromatography to give 0.70 grams (33% yield) of 2-benzylnicotinic acid as a white solid. Characteristic analytical data are as follows: mp 180°–182.5° C.; TLC in 20:1.8:0.2 (EtOAc/MeOH/HOAc); $^1$H NMR (DMSO-d$_6$, 300 MHz) δ4.50 (s, 2H), 7.12–7.48 (m, 5H), 8.18 (dd, 1H, J=8.0, 1.6 Hz), 8.63 (dd, 1H, J=4.8, 1.5 Hz); $^{13}$C NMR (75 MHz, DMSO-d$_6$) δ167.84, 160.17, 151.55, 139.85, 138.38, 128.75, 128.04, 126.37, 125.79, 121.57, 41.35, 39.76; mass spectrum (EI), m/e 213.

B. Formula 4 where $R_2$ is 3-chlorophenyl

Methyl 2-(3-chlorobenzoyl)-nicotinate (6.45 g., 23.4 mmoles) was dissolved in 300 ml ammonium hydroxide, to which was then carefully added a catalytic amount of copper(II) sulfate (190 mg, 1.2 mmoles), and zinc powder (15.6 g., 239 mmoles). The mixture was then refluxed for six days. The reaction mixture was filtered through a pad of celite, acidified to pH 5 with 1N HCl, then exhaustively extracted with ethyl acetate, washed brine and dried over sodium sulfate and filtered. Concentratiion under vacuum gave 2.55 grams (44% yield) of 2-(3-chlorophenyl) nicotinic acid.

C. Compounds of Formula 4 where $R_2$ is varied

By following the procedures described in Part A of this Example and substituting for methyl 2-benzoylnicotinate with other compounds of Formula 3 (where $R_2$ is varied as indicated in Table II of Example 1C above) there are obtained the corresponding substituted 2-benzylnicotinate compounds of Formula 4.

EXAMPLE 3

PREPARATION OF 8-PHENYLPYRANO [3,4-b]PYRIDIN-5-ONES

A. Formula 5 where $R_2$ is phenyl

To a solution of 2-benzylnicotinic acid (2.0 g., 9.4 mmoles) in 20 ml DMF was added dimethylformamide dimethyl acetal (3.1 ml, 23.5 mmoles). The mixture was heated to 80° C. overnight under nitrogen. The reaction mixture was cooled and concentrated under vacuum to give 2.39 grams of crude material. The crude material was chromatographed 1:4 (EtOAc/Hex) to give 1.05 grams (50% yield) of the desired 8-phenylpyrano[3,4b]pyridin-5-one as a white powder. Characteristic analytical data are as follows: mp 148°–149° C.; TLC 1:4 EtOAc/Hex; $^1$H NMR (CDCl$_3$, 300 MHz) δ7.4–7.6 (m, 7H), 8.64 (dd, 1H, Z=8.1, 1.9 Hz), 9.00 (dd, 1H, J=4.6, 2.0 Hz); $^{13}$C NMR (75 MHz, CDCl$_3$) δ162.08, 155.90, 146.09, 138.11, 131.94, 129.91, 128.55, 123.38, 122.20, 118.09; IR (KBr) v$_{max}$ 3630, 3441, 1741, 1626, 1556, 1496, 1462, 1437, 1286, 1261, 1236, 1197, 1105, 1062, 1016, 794, 758, 721, 694, 596 cm$^{-1}$; mass spectrum (EI), m/e 223. Anal. (C$_{14}$H$_9$NO$_2$) Calcd.: C, 75.33; H, 4.06; N, 6.27. Found: C; 75.38; H, 3.89; N, 6.41.

B. Formula 5 where $R_2$ is 3-chlorophenyl

To a solution of 2-(3-chlorophenyl) nicotinate acid (2.55 g, 10.3 moles) in 15 ml of DMF was added dimethylformamide dimethyl acetal (2.05 ml, 15.4 moles). The mixture was heated for two hours under nitrogen. The reaction mixture was cooled, concentrated under vacuum and chromatographed eluting with 1:4 ethyl acetate/hexanes to give 1.52 grams (57% yield ) of the desired 8-(3-chlorophenyl)pyrano [3,4-b]pyridin-5-one as a white powder. Characteristic analytical data are as follows: mp 158°–159.5° C; $^1$H NMR (CDCl$_3$, 300 MHz) δ7.28 (s, 1H) , 7.42–7.59 (m, 6H), 8.64 (dd, 1H, J=8.0, 1.8), 9.00 (dd, 1H, J=4.7, 1.9); $^{13}$C NMR (75 MHz, CDCl$_3$) δ161.74, 155.91, 152.78, 146.38, 138.16, 134.34, 133.69, 130.00, 129.73, 128.62, 128.06, 123.59, 121.07, 118.04; mass spectrum (EI), m/e 257. Anal. (C$_{14}$H$_8$ClNO$_2$) Calcd.: C, 65.26; H, 3.13; N, 5.44. Found: C, 65.04; H, 3.09; N, 5.51.

C. Compounds of Formula 5 where $R_2$ is varied.

By following the procedures described in Part A of this Example and substituting for 2-benzylnicotinic acid with other compounds of Formula 4 (where $R_2$ is varied as indicated in Table II of Example 1C) there are obtained the corresponding substituted pyrano[3,4-b]pyridinone compounds of Formula 5.

EXAMPLE 4

PREPARATION OF 8-SUBSTITUTED-1,6-NAPHTHYRIDIN-5-ONES

A. Formula I where $R_1$ is hydrogen and $R_2$ is phenyl

To a solution of 8-phenylpyrano[3,4-b]pyridin-5-one (340 mg, 1.5 moles) in 10 ml DMF was added solid ammonium acetate (180 mg, 2.3 mmoles). The solution was heated to 80° C. under nitrogen for 18 hours, cooled and concentrated under vacuum. The solution was then flashed chromatographed eluting with ethyl acetate to give 245 mg (73% yield) of the desired 8-phenyl-1,6-naphthyridin- 5-one as a white solid. Characteristic analytical data are as follows: mp 260°–263° C.; $^1$H NMR (DMSO-d$_6$, 300 MHz) δ7.38–7.65 (m, 7H), 8.64 (dd, 1H, J=8.1, 1.8 Hz), 8.98 (dd, 1H, J=4.5, 2.0 Hz), 11.83 (b, 1H); $^{13}$C NMR (75 MHz, DMSO-d$_6$) δ 161.72, 153.98, 152.24, 135.55, 131.56, 129.93, 127.79, 126.77, 121. 62, 118.43; mass spectrum (EI), m/e 222.

B. Formula I where $R_1$ is hydrogen and $R_2$ is 3-chlorophenyl

To a solution of 8-(3-chlorophenyl)pyrano [3,4-b]pyridin-5-one (1.25 g., 4.9 mmoles) in 20 ml DMF was added solid ammonium acetate (0.56 g., 7.29 mmoles). The reaction was heated at 50° C. under nitrogen for one hour, cooled and concentrated under vacuum. The solid was triturated with ether to give 1.1 grams (88% yield) 8-(3-chlorophenyl)-1, 6-naphthyridin-5-one as a white solid. Characteristic analytical data are as follows: mp 252°–252.5° C.; $^1$H NMR (DMSO-d$_6$, 300 MHz) δ7.37–7.66 (m, 6H), 8.58 (dd, 1H, J=8.2, 2.1), 8.94 (dd, 1H, J=4.69, 1.68), 11.85 (bs, 1H); $^{13}$C NMR (75 MHz, DMSO-d$_6$) δ161.74, 154.04, 151.91, 137.69, 135.62, 132.47, 132.26, 129.68, 129.55, 128.43, 126.64, 121.85, 121.60, 116.87; IR (KBr) v$_{max}$ 3437, 3173, 3032, 2951, 2878, 1672, 1630, 1593, 1566, 1477, 1462, 1417, 1340, 1236, 821, 794, 692, 671, 603, 555 cm$^{-1}$; mass spectrum (EI), m/e 256. Anal. (C$_{14}$H$_9$ClN$_2$O) Calcd.: C, 65.51; H, 3.53; N, 10.91; Cl, 13.81. Found: C, 65.67; H, 3.34; N, 10.98; Cl, 13.91.

C. Compounds of Formula I where $R_2$ is varied

By following the procedures described in Part A of this Example and substituting 8-phenylpyrano [3,4-b]pyridin-5-one with other compounds of Formula 5 (where $R_2$ is varied as indicated in Table II of Example 1C) there are obtained the corresponding 8-substituted- 1,6-naphthyridin-5-ones of Formula I (where $R_1$ is hydrogen).

EXAMPLE 5

PREPARATION OF 6-SUBSTITUTED-8-PHENYL-1,6-NAPHTHYRIDIN-5-ONES BY CONDENSATION OF PYRANO [3,4-b]PYRIDIN-5-ONES WITH AMINES

A. Formula I where $R_1$ is benzyl.

To a solution of 8-phenylpyrano [3,4-b]pyridin-5-one (100 mg, 0.45 mmoles) in 5 ml DMF was added benzylamine (0,006 ml, 0.54 mmoles) under nitrogen. The reaction mixture was heated overnight to 80° C., cooled and concentrated under vacuum to give 253 mg of crude product. The crude product was chromatographed eluting with 1:1 EtOAc/Hexanes to give 72 mg (51% yield) of the desired 6-benzyl-8-phenyl-1,6-naphthyridin-5-one as a white solid. Characteristic analytical data are as follows: mp 166°–167° C.; $^1$H NMR (CDCl$_3$, 300 MHz) δ5.31 (s, 2H), 7.28–7.58 (m, 12H) 8.82 (dd, 1H, J=8.2, 1.8 Hz) 8.98 (dd, 1H, J=4.6, 2.0 Hz); $^{13}$C NMR (75 MHz, CDCl$_3$) δ161.88, 154.10, 151.84, 137.00, 136.29, 135.06, 134.24, 130.02, 129.02, 128.40, 128.19,128.12, 127.77, 122.06, 121.09,120.99, 52.00; mass spectrum (CI) , m/e 312; exact mass calcd. for C$_{21}$H$_{16}$N$_2$O 312.1263, found 312.1259.

B. Formula I where $R_1$ is 4-pyridylmethyl

To a solution of 8 -phenylpyrano [3,4-b]pyridin-5-one (102 mg, 0.46 mmoles) in 2 ml DMF was added 4-picolylamine (0.055 ml, 0.55 mmoles) under nitrogen. The reaction mixture was heated overnight to 80° C., cooled and then concentrated under vacuum to give 0,335 g crude product which was chromatographed eluting with 1:1 ethyl acetate/ hexanes to give 69 mg (48% yield) of the desired 6-(4-pyridylmethyl)-8-phenyl-1,6-naphthyridin-5-one as a white solid. Characteristic analytical data are as follows: mp 199.5°–200.5° C.; $^1$H NMR (CDCl$_3$,300 MHz) δ5.30 (s, 2H), 7.26 (d, 2H, J=6), 7.34–7.59 (m, 7H), 8.6 (d, 2H, J=6), 8.78 (dd, 1H, J=8.04, 2.00), 8.99 (dd, 1H, J=4.39, 1.83); $^{13}$C NMR (75 MHz, CDCl$_3$) δ161.90, 154.52, 152.09, 150.08, 145.44, 136.72, 134.77, 133.67, 129.96, 128.40, 127.92, 122.44, 122.16, 121.90, 121.81, 51.18; IR (KBr) $v_{max}$ 3445, 1655, 1624, 1599, 1437, 1421, 1373, 1169, 1099, 993,922, 868, 794, 763, 727, 707, 677, 607, 598, 522 cm$^{-1}$; mass spectrum (EI), m/e 313. Anal. (C$_{20}$H$_{15}$N$_3$O ¾ H$_2$O) Calcd.: C, 73.49; H, 5.09; N, 12.86. Found: C, 73.73; H, 4.99; N, 12.36.

EXAMPLE 6

PREPARATION OF 6-SUBSTITUTED-8-PHENYL-1,6-NAPHTHYRIDIN-5-ONES BY ALKYLATION WITH AN ALKYL HALIDE

A. Formula I Where R$_2$ is ethyl

To a solution of 8-phenyl-1,6-naphthyridin-5-one (142 mg, 0.6 moles) in 5 ml DMF was added solid potassium carbonate. The resulting suspension was stirred under nitrogen at 21° C. for 30 minutes. Iodoethane (0.13 ml, 1.6 moles) was added and the reaction mixture heated overnight to 80° C. The mixture was cooled and concentrated under vacuum, and chromatographed by silica gel [column chromatography, eluting with 1:1 ethyl acetate/hexanes] to give 70 mg (47% yield) of the desired 6-ethyl- 8-phenyl-1,6-naphthyridin-5-one as a white solid. Characteristic analytical data are as follows: mp 141.5°–141.7° C.; $^1$H NMR (CDCl$_3$, 300 MHz) δ1.44 (t, 3H, J=7.2 Hz), 4.12 (q, 2H, J=7.2 Hz), 7.38–7.63 (m, 7H), 8.78 (dd, 1H, J=8.1, 2.0 Hz), 8.95 (dd, 1H, J=4.6, 1.8 Hz); $^{13}$C NMR (75 MHz, CDCl$_3$) δ161.59, 154.09, 151.99, 136.51, 135.38, 134.01, 129.98, 128.38, 127.66, 121.96, 121.74, 120.98, 44.52, 14.67; IR (KBr) $v_{max}$ 1647, 1620, 1597, 1587, 1550, 1498, 1437, 1375, 1298, 1246, 1178, 1169, 792, 758, 726, 694, 626, 598, 499, 455 cm$^{-1}$; mass spectrum (EI), m/e 250. Anal. (C$_{16}$H$_{14}$N$_2$O) Calcd.: C, 76.78; H, 5.64; N, 11.19. Found C, 76.78; H, 5.61; N, 11.18.

EXAMPLE 7

PREPARATION OF 6-SUBSTITUTED-8-(3-CHLOROPHENYL)-1,6-NAPHTHYRIDIN-5-ONES BY ALKYLATION WITH AN ALKYL HALIDE

A. Formula I Where R$_1$ is ethyl

To a suspension of 8-(3-chlorophenyl)-1,6-naphthyridin-5-one (128 mg, 0.5 moles) and potassium carbonate (83 mg, 0.6 moles) in 10 ml DMF was added dropwise iodoethane (0.06 ml, 0.75 moles) under an atmosphere of nitrogen. The reaction mixture was stirred overnight at 21° C. The mixture was poured into 50 ml water and after stirring for one hour a white precipitate was collected and dried. Crystallization from ether/hexanes gave 117 mg (82% yield) of the desired 6-ethyl-8-(3-chlorophenyl)-1,6-naphthyridin-5-one as a white solid. Characteristic analytical data are as follows: mp 127°–128° C.; TLC 1:4 EtOAc/Hex; $^1$H NMR (CDCl$_3$, 300 MHz) δ1.42 (t, 3H, J= 7.2), 4.11 (q, 2H, J=7.2), 7.35–7.60 (m, 6H), 8.76 (dd, 1H, J=8.0, 1.9), 8.93 (dd, 1H, J=4.5, 1.8); $^{13}$C NMR (75 MHz, CDCl$_3$) δ161.54, 154.13, 151.62, 137.15, 136.60, 134.29, 134.16, 129.96, 129.53, 128.24, 127.70, 121.95, 119.63, 108.46, 44.62, 14.67; IR (KBr) $v_{max}$ 3439, 1647, 1622, 1591, 1564, 1552, 1483, 1458, 1439, 1417, 1375, 1298, 1176, 1167, 1099, 794, 729, 711, 696, 603 cm$^{-1}$; mass spectrum (EI), m/e 284. Anal. (C$_{16}$H$_{13}$ClN$_2$O .⅛ H$_2$O) Calcd.: C, 66.96; H, 4.57; N, 9.76. Found: C, 66.82; H, 4.55; N, 9.61.

B. Formula I Where R$_1$ is 2-Propyl

To a suspension of 8-(3-chlorophenyl)-1,6-naphthyridin-5-one (128 mg, 0.5 mmoles) and potassium carbonate (83 mg, 0.6 mmoles) in 10 ml DMF was added dropwise 2-iodopropane (0.075 ml, 0.75 mmoles) under an atmosphere of nitrogen and stirred overnight at 21° C. The reaction mixture was poured into 50 ml water and after stirring for one hour the white precipitate was collected and dried. Crystallization from methanol gave 60 mg (40% yield) of the desired 6-(2-propyl)-8-(3-chlorophenyl)-1,6-naphthyridin- 5-one as a white solid. Characteristic analytical data are as follows: mp 163.5°–164.5° C.; TLC 1:4 EtOAc/Hex; $^1$H NMR (CDCl$_3$, 300 MHz) δ1.454 (d, 6H, J=6.8), 5.3 (m, 1H, J=6.8), 7.36–7.60 (m, 6H), 8.77 (dd, 1H, J=8.3, 1.7), 8.93 (dd, 1H, J=4.4, 1.7); $^{13}$C NMR (75 MHz, CDCl$_3$) δ154.20, 151.13, 137.54, 136.85, 134.18, 129.99, 129.55, 128.28, 127.69, 121.95, 119.70, 46.57, 21.87; IR (KBr) $v_{max}$ 1647, 1614, 1591, 1566, 1552, 1487, 1468, 1441, 1419, 1400, 1388, 1273, 1242, 1182, 1170, 796, 783, 711, 700, 605 cm$^{-1}$; mass spectrum (EI), m/e 298. Anal. (C$_{17}$H$_{15}$ClN$_2$O) Calcd.: C, 68.34; H, 5.06; N, 9.38. Found: C, 68.25; H, 5.11; N, 9.38.

C. Formula I where R$_1$ is 4-pyridylmethyl

To a suspension of 8-(3-chlorophenyl)-1,6-naphthyridin-5-one (128 mg, 0.5 mmoles) and potassium carbonate (346 mg, 2.5 mmoles) in 20 ml DMF was added solid 4-picolyl chloride.HCl (164 mg, 1.0 mmole) under an atmosphere of nitrogen and stirred overnight at 21° C. The reaction mixture was poured into 100 ml water and after stirring for one hour the white precipitate was collected and dried. Crystallization from methanol gave 84 mg (48% yield) of the desired 6-(4-pyridylmethyl)-8-(3-chlorophenyl)-1,6-naphthyridin-5-one as a white solid. Characteristic analytical data are as follows: mp 170.5°–172.5° C.; TLC in 1:1 EtOAc/Hex; $^1$H NMR (CDCl$_3$, 300 MHz) δ5.20 (s, 2H), 7.15 (dd, 2H, J=4.7, 1.5), 7.28–7.50 (m, 6H), 8.52 (dd, 2H, J=4.4, 1.5), 8.69 (dd, 1H, J=8.1, 2.1), 8.90 (dd, 1H, J=4.7, 1.8); $^{13}$C NMR (75 MHz, CDCl$_3$) δ161.86, 154.58, 151.75, 150.46, 144.94, 136.83, 136.59, 134.20, 134.01, 130.01, 129.58, 128.23, 127.98, 122.37, 122.32, 121.93, 120.47, 51.25; IR (KBr) $v_{max}$ 3435, 3051, 1668, 1630, 1591,1552, 1483, 1415, 1367, 1358, 1342, 1292, 1097, 997, 827, 794, 729, 702, 601, 472 cm$^{-1}$; mass spectrum (EI), m/e 347. Anal. (C$_{20}$H$_{14}$ClN$_3$O.⅜) Calcd.: C, 67.75; H, 4.19; N, 11.85; Cl, 9.99. Found: C, 67.95; H, 4.09; N, 11.84; Cl, 9.99.

D. Formula I Where R$_1$ is benzyl

To a suspension of 8-(3-chlorophenyl)-1,6-naphthyridin-5-one (200 mg, 0.78 mmoles) and potassium carbonate (130 mg, 0.93 mmoles) in 10 ml DMF was added dropwise benzyl bromide (0.14 ml, 1.2 mmoles) under an atmosphere of nitrogen and stirred overnight at 21° C. The reaction mixture was poured into 100 ml water and after stirring for one hour the white precipitate was collected and dried. Crystallization from methanol gave 151 grams (56% yield) of the desired 6-benzyl-8-(3-chlorophenyl)-1,6-naphthyridin-5-one as a white solid. Characteristic analytical data are as follows: mp 148.8°–150° C.; TLC in 1:4 EtOAc/Hex; $^1$H NMR (CDCl$_3$, 300 MHz) δ5.28 (s, 2H), 7.30–7.55 (m, 10H), 8.78 (dd, 1H, J=8.1, 1.9), 8.94 (dd, 1H, J=4.5, 1.9); $^{13}$C NMR (75 MHz, CDCl$_3$) δ154.31, 151.66, 136.97, 136.84, 136.17, 134.30, 134.13, 130.02, 129.51, 129.05, 128.23, 128.07, 127.77, 122.10, 122.01,119.86, 52.04; IR (KBr) $v_{max}$ 1645, 1612, 1589, 1552, 1483, 1460, 1439, 1417, 1369, 1304, 1294, 1197, 1170, 790, 744, 729, 713, 702, 692, 599 cm$^{-1}$; mass spectrum (EI), m/e 346. Anal. ($C_{21}H_{15}ClN_2O$) Calcd.: C, 72.73; H, 4.36; N, 8.08. Found: C, 72.61; H, 4.35; N, 8.14.

E. 6, 8-disubstituted-1,6-naphthyridin-5-ones where $R_2$ is varied

By following the procedures of Parts A-D of this Example and substituting for 8-(3-chlorophenyl)-1,6-naphthyridin-5-one with the compounds obtained in Example 4C (where $R_2$ is varied as described in Table II of Example 1C) are obtained the corresponding 6,8-disubstituted-1,6-naphthyridin-5-ones.

EXAMPLE 8

PREPARATION OF 6-SUBSTITUTED -8-(3-CHLOROPHENYL)-1,6-NAPHTHYRIDIN-5-ONES USING TRIPHENYLPHOSPHINE, DIAD AND AN ALCOHOL

A. Formula I where $R_2$ is 2-Furfuryl

To a suspension of 8-(3-chlorophenyl)-1,6-naphthyridin-5-one (128 mg, 0.5 mmoles), furfuryl alcohol (0.05 ml, 0.6 mmoles), and triphenylphosphine (197 mg, 0.75 mmoles) was added dropwise diisopropylazodicarboxylate (0.15 ml, 0.75 mmoles) under an atmosphere of nitrogen at 21° C. The reaction mixture was stirred overnight and concentrated under vacuum to give an oil. The oil was chromatographed with silica gel (eluting with 1:4 ethyl acetate/hexane) to give (after crystallization from methanol) 46 mg (27% yield) of the desired 6-(2-furfuryl)-8-(3chlorophenyl) -1,6-naphthyridin-5-one as a white solid. Characteristic analytical data are as follows: mp 111°–112.5° C.; $^1$H NMR (CDCl$_3$, 300 MHz) δ5.18 (s, 2H), 6.29–6.42 (m, 2H), 7.28–7.50 (m, 6H), 8.69 (dd, 1H, J=8.1, 1.8), 8.86 (dd, 1H, J =4.5, 2.0); $^{13}$C NMR (75 MHz, CDCl$_3$) δ161.56, 154.31, 148.97, 143.21, 136.99, 136.78, 134.14, 134.00, 130.05, 129.53, 128.24, 127.78, 122.06, 121.93, 119.73, 110.78, 110.00, 44.52, 1.04; IR (KBr) v$_{max}$ 3437, 1655, 1620, 1591, 1554, 1481, 1417, 1365, 1261, 1186, 1169, 1149, 1099, 1018, 794, 767, 750, 715, 696, 601 cm$^{-1}$; mass spectrum (EI), m/e 336. Anal. ($C_{19}H_{13}ClN_2O_2 \cdot CH_3OH$) Calcd.: C, 65.13; H, 4.65; N, 7.60. Found: C, 64.86; H, 4.48; N, 7.26.

B. Formula I where $R_1$ is 2-thienylmethyl

To a suspension of 8-(3-chlorophenyl)-1,6-naphthyridin-5-one (128 mg, 0.5 mmoles), thiophenemethanol (0.08 ml, 0.6 mmoles), and triphenylphosphine (197 mg, 0.75 mmoles) was added dropwise diisopropylazodicarboxylate (0.15 ml, 0.75 mmoles) under an atmosphere of nitrogen at 21° C. The reaction mixture was stirred overnight and concentrated under vacuum to give an oil. The oil was chromatographed with silica gel (eluting with 1:4 ethyl acetate/hexane) to give (after crystallization from methanol) 98 mg (56% yield) of the desired 6-(2-thienylmethyl)-8-(3-chlorophenyl)-1,6-naphthyridin-5-one as a white solid: mp 141.5°–145.0° C; $^1$H NMR (CDCl$_3$, 300 MHz) δ5.41 (s, 2H), 6.97–7.56 (m, 9H), 8.78 (dd, 1H, J=8.1, 1.9), 8.93 (dd, 1H, J=4.5, 1.9); $^{13}$C NMR (75 MHz, CDCl$_3$) δ161.56, 154.34, 151.68, 137.91, 136.93, 136.79, 134.14, 133.70, 130.04, 129.54, 128.26, 127.81, 127.77, 127.09, 126.65, 122.13, 121.91, 120.05, 46.85; IR (KBr) v$_{max}$ 1643, 1612, 1591, 1564, 1552, 1483, 1441, 1429, 1415, 1377, 1358, 1302, 1207, 1174, 792, 763, 734, 715, 696, 601 cm$^{-1}$; mass spectrum (EI), m/e 352. Anal. ($C_{19}H_{13}ClN_2OS$) Calcd.: C, 64.68; H, 3.71; N, 7.94. Found: C, 64.45; H, 3.69; N, 8.00.

C. Formula I Where $R_1$ is cyclopropylmethyl

To a suspension of 8-(3-chlorophenyl)-6-naphthyridin-5-one (107 mg, 0.42 mmoles), cyclopropane methanol (0.04 ml, 0.5 mmoles), and triphenylphosphine (164 mg, 0.5 mmoles) was added dropwise diisopropylazodicarboxYlate (0.12 ml, 0.625 mmoles) under an atmosphere of nitrogen at 21° C. The reaction mixture was stirred overnight and concentrated under vacuum to give an oil. The oil was chromatographed with silica gel (eluting with 1:4 ethyl acetate/hexane) to give (after crystallization from methanol) 54 mg (41% yield) of the desired 6-cyclopropylmethyl-8-(3-chlorophenyl)-1,6-naphthyridin-5-one as a white solid. Characteristic analytical data are as follows: mp 119.8°–22.0° C.; $^1$H NMR (CDCl$_3$, 300 MHz) δ0.45–1.32 (m, 5H) , 3.95 (d, H, J=7.1), 7.38–7.60 (m, 6H), 8.78 (d, 1H, J=6.2), 8.94 (d, 1H, J=2.8); $^{13}$C NMR (75 MHz, CDCl$_3$) δ154.16, 136.69, 34.45, 130.00, 129.54, 128.24, 127.68, 121.91, 53.44, 10.79, 4.04; IR (KBr) v$_{max}$ 3435, 3063, 1645, 1618, 1591, 1552, 1485, 439, 1417, 1373, 1294, 1240, 1163, 1095, 1022, 790, 725, 694, 65, 603 c$^{-1}$; mass spectrum (EI), m/e 310. Anal. ($C_{18}H_{15}ClN_2O \cdot \frac{3}{4} H_2O$) Calcd.: C, 66.67; H, 5.12; N, 8.64. Found: C, 66.87; H, 5.07; N, 8.66.

D. Formula I Where $R_1$ is cyclopentylmethyl

To a suspension of 8-(3-chlorophenyl)-1,6-naphthyridein-5-one (118 mg, 0.46 mmoles), cyclopentane methanol (0.06 ml,0.55 mmoles), and triphenylphosphine (181 mg, 0.69 moles) was added dropwise diisopropylazodicarboxylate (0.14 ml, 0.69 mmoles) under an atmosphere of nitrogen at 21° C. The reaction mixture was stirred overnight and concentrated under vacuum to give an oil. The oil was chromatographed with silica gel (eluting with 1:4 ethyl acetate/hexane) to give (after crystallization from methanol) 40 mg (26% yield) of the desired 6-cyclopentylmethyl-8-(3-chlorophenyl)-1,6-naphthyridin-5-one as a white solid. Characteristic analytical data are as follows: mp 122.5°–123.5° C.; $^1$H NMR (CDCl$_3$, 300 MHz) δ1.31–1.81 (m, 8H), 2.41 (q, 1H, J=7.6), 4.02 (d, 2H, J=7.6), 7.26–7.60 (m, 6H), 8.75 (dd, 1H, J=8.2, 1.8), 8.93 (dd, 1H, J=4.6, 1.8); $^{13}$C NMR (75 MHz, CDCl$_3$) δ154.14, 137.19, 136.72, 135.04, 134.15, 129.99, 129.53, 128.24, 127.68, 121.91, 53.92, 39.96, 30.38, 24.87; IR (KBr) v$_{max}$ 3439, 2951, 1651, 1591, 1483, 1414, 1379, 1294, 1170, 1020, 794, 696, 603 cm$^{-1}$; mass spectrum (EI), m/e 338. Anal. ($C_{20}H_{19}ClN_2O \cdot \frac{1}{8}H_2O$) Calcd.: C, 70.42; H, 5.64; N, 8.21. Found: C, 70.43; H, 5.65; N, 8.26.

E. 6,8-disubstituted-1,6-naphthyridin-5-ones where $R_2$ is varied

By following the procedures of Parts A-D of this Example and substituting for 8-(3-chlorophenyl)-1,6-naphthyridin-5-one with the compounds obtained in Example 4C (where $R_2$ is varied as described in Table II of Example 1C) are obtained the corresponding 6,8-disubstituted-1,6-naphthyridin-5-ones.

EXAMPLE 9

Determination of Potency and Selectivity of Inhibitors for PDE IV

Preparation of Human Platelet Phosphodiesterase (PDE III)

Platelet high-affinity cAMP PDE (PDE III) was obtained from human blood in accordance with previously described procedures described in *Mol. Pharmacol.* 20:302–309, Alvarez, R., Taylor, A., Fazarri, J. J., and Jacobs, J. R. (1981).

Blood was collected into evacuated tubes containing EDTA (7.7 mM, final concentration). PRP was obtained by centrifuging the blood in polycarbonate tubes at 200×g for 15 min at 4° C. A platelet pellet was resuspended in a volume of buffer A (0.137M NaCl 12.3 mM Tris-HCl buffer, pH 7.7, containing 1 mM $MgCl_2$. The hypotonically-lysed platelet suspension was centrifuged at 48,000×g for 15 min and the supernatant was saved. The pellets were frozen on dry ice and briefly thawed at 22° C. The supernatant was combined with the pellet fraction and the resulting suspension was centrifuged at 48,000× g for 30 min. The supernatant fraction was stored in 0.5 mL aliquots at −20° C. and used as the soluble PDE. Enzyme activity was adjusted to 10–20% hydrolysis after 10 minutes of incubation by dilution with 10mM cold Tris-HCl buffer, pH7.7.

Preparation of Human Lymphocyte Phosphodiesterase (PDE IV)

Human B cell line (43D) were cultured at 37° C. in 7% $CO_2$ in RPMI 1640 with L-glutamine and 10% Nu-Serum. Prior to the assay ~1.5×10$^8$ cells were centrifuged at 1000 rpm for 10 minutes in a table top clinical centrifuge. The pellet was resuspended in 2–3 mL of 45 mM Tris-HCl buffer, pH 7.4. The suspension was homogenized and centrifuged at 12,000×g 4° C. for 10 minutes. The supernatant was diluted to 28 mL with Tris-HCl buffer and used directly in the assay or stored at −20° C. The final concentration of DMSO in the PDE incubation medium was 1%. Nitraquazone was included in each assay (10 and 100 µM) as a reference standard.

Human Platelet cAMP Phosphodiesterase Assay

The phosphodiesterase incubation medium contained 10 mM Tris-HCl buffer, pH 7.7, 10 mM $MgSO_4$, 0.1–1 µM [$^3$H]-AMP (0.2 µCi) in a total volume of 1.0 mL. Following addition of the enzyme, the contents were mixed and incubated for 10 min at 30° C. The reaction was terminated by immersing the tubes in a boiling-water bath for 90 sec. After the tubes were cooled in an ice-water bath, 0.1 mL (100 µg) of 5'-nucleotidase from snake venom (Crotalus atrox, Sigma V-7000) was added to each tube. The contents were mixed and incubated for 30 min at 30° C. The nucleotidase reaction was terminated by immersing the tubes in a boiling water bath for 60 sec. Labeled adenosine was isolated from alumina columns according to the method described in *Anal. Biochem.*, 52:505–516 (1973), Filburn, C. R., and Karn, J. Assays were performed in triplicate. Hydrolysis of cAMP ranged from 10–20%. Test compounds were dissolved in DMSO. The final concentration of DMSO in the phosphodiesterase assay was 1% when tested with compounds up to 0.1 mM. When tested at 1 mM the DMSO concentration was 10% and this activity was compared to control PDE activity in the presence of 10% DMSO.

Human Lymphocyte cAMP Phosphodiesterase Assay

The phosphodiesterase incubation medium contained 40 mM Tris-HCl buffer, pH 7.7, 0.1 mM $MgSO_4$, 3.75 mM mercaptoethanol, and 0.1–1.0 µM [$^3$H] cAMP (0.2 µCi) in a total volume of 1.0 mL. The reaction was performed and processed according to the procedure used (above) for human platelet PDE. The final concentration of DMSO was 1%.

The representative compounds of the present invention exhibit potency and selectivity as inhibitors of PDE IV when tested by the human platelet cAMP phosphodiesterase assay and the human lymphocyte cAMP phosphodiesterase assay.

EXAMPLE 10

Determination of Immunosuppressive Activity Utilizing Responses of Human Peripheral Blood Lymphocytes to Mitogen This procedure is a modification of a procedure initially described by Greaves, et al. ["Activation of human T and B lymphocytes by polyclonal mitogens," *Nature*, 248, 698–701 (1974)].

Human mononuclear cells (PBL) were separated from heparinized whole blood by density gradient centrifugation in Ficoll-Paque (Pharmacia). After washing, 5×10$^4$ cells/well are cultured in microtiter plates with minimal essential media supplemented with 1% human serum, gentamicin, sodium bicarbonate, 2-mercaptoethanol, glutamine, nonessential amino acids, and sodium pyruvate. The mitogen concanavalin A (Sigma) is used at a concentration of 2 µg/ml. Test materials are tested at concentrations between $10^{-4}$ and $10^{-10}$M, by addition to the culture at time 0. Cultures are set up in quadruplicate and incubated at 37° C. in a humidified atmosphere with 5% $CO_2$ for 48 hours. A pulse of 1.0 µCi/well of $^3$H-thymidine is added for the last 4 hours. Cells are collected on glass fiber filters with an automatic harvester and radioactivity is measured by standard scintillation procedures. The 50% inhibitory concentration ("IC$_{50}$") for mitogenic stimulation is determined graphically.

The representative compounds of the present invention showed immunosuppressive activity when tested by this method.

EXAMPLE 11

Determination of Immunosuppressive Activity Utilizing The Hemolytic Plaque Forming Cell Assay This procedure is a modification of "The agar plaque technique for recognizing antibody producing cells," a procedure initially described by Jerne, et al. [*Cell-bound Antibodies*, Amos and Kaprowski editors (Wistar Institute Press, Philadelphia, 1963) p. 109].

Groups of 5–6 adult C3H female mice were sensitized with 1.25×10$^8$ sheep red blood cells (SRBC) and simultaneously treated with an oral dosage form of the test material in an aqueous vehicle. Animals in a control group receive the same volume of vehicle. Four days after SRBC inoculation, spleens are dispersed in glass homogenizers. The number of nucleated cells (WBC) is determined and the spleen cell suspension is mixed with SRBC, guinea pig complement and agar solution at 0.5% concentration. Aliquots of the above mixture (0.1 mL) are dropped on four separate quadrants of a Petri dish and are covered with cover slips. After two hours incubation at 37° C., areas of hemolysis around plaque-forming cells (PFC) are counted with a dissecting microscope. Total WBC/spleen, PFC/spleen and PFC/10$^6$ WBC (PPM) are calculated for each mouse spleen. Geometric means of each treatment group are then compared with the vehicle-treated control group.

The representative compounds of the present invention showed immunosuppressive activity when tested by this method,

EXAMPLE 12

Determination of Anti-Inflammatory Activity Utilizing Arachidonic Acid-Induced Ear Edema in the Mouse This procedure is a modification of a procedure described by Young et al., *J. Invest. Derm.*, 82:367–371 (1984).

Female Charles River ICR mice 23–27 grams are administered 0.2 mL of test material. The mice are later challenged with 20 µl of arachidonic acid applied topically to the ear.

One hour after challenge, the weight of an 8 mm disc is determined. The mean increase in ear plug weight is calculated. Materials with anti-inflammatory activity inhibit the increase in ear plug weight.

The representative compounds of the present invention exhibited anti-inflammatory activity when tested by this method,

EXAMPLE 13

Determination of Anti-Inflammtory Activity Utilizing Adjuvant-Induced Arthritis In The Rat This procedure is a modification of a procedure initially described by Pearson, C. M., *Proc. Soc. Exp. Biol. Med.,* 91:95–101 (1956).

Female Charles River albino rats weighing 160–180 g receive 0.1 mL of a suspension in paraffin oil of heat-killed *Mycobacterium butyricum* (10 mg/ml) by means of an intradermal injection into the proximal ¼ of the tail on day 0. Beginning on day 1, the test material is administered orally in an aqueous vehicle (0.5 mL/dose) once each day for 17 days. On day 18 the intensity of the swelling of the four foot pads and tail is determined utilizing a scoring system in which the swelling in the four paws was scored 0–4 for each paw and the tail swelling is scored 0–3, such that the total maximum score is 19.

The representative compounds of the present invention exhibit anti-inflammatory activity when tested by this method.

EXAMPLE 14

Determination of Activity Towards Autoimmune Disease Utilizing Survival of MRL/lpr Mice MRL/lpr mice develop a multisystemic disease characterized by glomerulonephritis, arthritis, arteritis, lymphoid hyperplasia. The length of survival of mice with this disease is approximately one-third that of non-disease developing MRL/n mice. These mice have a high incidence of autoantibodies and the disease process is considered autoimmune in nature as described by Theofilopoulos, et al., *Advances in Immunology,* 37:269–390 (1985).

The representative compounds of the present invention significantly extend the lifespan of the MRL/lpr mice.

EXAMPLE 15

Determination of Analgetic Activity Utilizing Phenylquinone-Induced Stretching in the Mouse This procedure is a modification of a procedure described by Hendershoot, et al. *J. Pharmacol. Exp. Ther.,* 125:237–240 (1959).

Groups of 8 Female CD-1 mice are administered test materials orally in an aqueous vehicle. At various times following administration of test materials, 0.25 mL of a 0.02% solution of phenylquinone is administered intraperitoneally. The number of stretches for each animal is enumerated over a ten minute period following the phenylquinone administration. Analgetic activity is determined by inhibition of the mean number of stretches.

Representative compounds of the present invention show analgetic activity when tested by this method.

EXAMPLE 16

Measurement of Bronchoconstriction and Cell Infiltration in the Airway Lumen of Guinea Pigs Following Antigert Challenge This procedure is a modification of a procedure initially described by Hutson et al., *American Review of Respiratory Disease,* 137, 548–557 (1988).

Groups of Male Dunkin-Hartley guinea pigs weighing 250–350 g are sensitized by exposure to aerosolized ovalbumin (2% wt/vol in 0.9% sterile sodium chloride) on two occasions separated by 7 days. The aerosol is generated by a Mallinckrodt Ultravent nebulizer driven by compressed air at approximately 6L/min. Under these conditions, the mass median particle diameter is 3.0 $\mu M$. The aerosol is generated into a 2.5 liter plexiglas chamber in which the animals are placed for 5 min on each occasion.

At least two weeks following sensitization, each animal is placed into a double chamber whole body plethysmograph (BUXCO Electronics, Troy, N.Y.) in which the head and body compartments are separated by a neck restrainer. The animals are challenged with an ovalbumin aerosol (2% wt/vol in 0.9% sodium chloride) following pretreatment with an oral dosage form of the test material in an aqueous vehicle. Animals in control groups received the same volume of vehicle. To protect the guinea pigs from the effects of histamine released during the immediate anaphylaxis following antigen challenge, the histamine H1-receptor antagonist, pyrilamine (10 mg/Kg) is administered intraperitoneally 30 minutes before challenge. Ventilatory parameters and specific airway resistance (sRaw) and conductance from the animals are analyzed and derived flow signals received from the separate nasal and thoracic compartments in the plethysmograph using a Non Invasive Airway Mechanics Pulmonary Analyzer (BUXCO Electronics, Troy, N.Y.). Each animal's airway parameters are recorded for at least 10 minutes prior to antigen challenge and at least 50 minutes following antigen challenge. The change in sRaw during the post-antigen challenge period is calculated utilizing its own pre-antigen challenge as control. The mean of this change in sRaw from each treatment group is then compared with the vehicle-treated control group.

The cellular infiltrate into the broncheoalveolar lumen associated with allergen-induced bronchoconstriction can be assessed by analysis of broncheoalveolar lavage (BAL) fluids. Approximately 24 hours following antigen challenge, guinea pigs are euthanized with an intraperitoneal injection of sodium pentobarbital (100 mg/Kg). A tracheostomy is performed, the trachea cannulated and the lungs layaged with 5 consecutive washes of 10 mL aliquots of Dulbecco's Phosphate Buffered Saline (D-PBS) instilled through the tracheal cannula by a syringe. The various aliquots of BAL fluids are pooled and the cells are pelleted by centrifugation at 1200 rpm for 10 minutes. The pellet is washed and then resuspended in RPMI cell media (GIBCO-BRL, Grand Island, NY)and the total number of cells following lysis of red blood cells is quantitated using a Coulter Counter. Visual differential leukocyte counts are undertaken on cytocentrifuged preparations of cell aliquots following staining with Giemsa eosin stain. A minimum of 300 cells are counted using standard morphologic criteria to classify the cells into neutrophils, eosinophils and mononuclear cells. The total number of eosinophils present in the BAL is calculated by multiplying the % eosinophils present in the differential count by the total number of cells recovered from the BAL.

Representative compounds of the present invention significantly inhibited the antigen-induced bronchoconstriction as well as total cell infiltration and eosinophilia in the airway lumen of antigen-sensitized guinea pigs.

EXAMPLE 17

Capsule Formulation

This example illustrates the preparation of a representative pharmaceutical formulation for oral administration containing an active compound of Formula I, e.g., 6-cyclopropylmethyl-8-(3-chlorophenyl)-1,6-naphthyridine-5-one.

| Ingredients | Quantity (mg/capsule) |
|---|---|
| Active compound | 200 |
| lactose, spray-dried | 148 |
| magnesium stearate | 2 |

The above ingredients are mixed and introduced into a hard-shell gelatin capsule.

Other compounds of Formula I, such as those prepared in accordance with Examples 1–8 can be used as the active compound in the preparation of the orally administrable formulations of this example.

EXAMPLE 18

Oral Formulation

This example illustrates the preparation of a representative pharmaceutical formulation containing an active compound of Formula I, e.g., 6-cyclopropylmethyl-8-(3-chlorophenyl)- 1,6-naphthyridine-5-one.

An suspension for oral administration is prepared having the following composition:

| Ingredients | Quantity |
|---|---|
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I, such as those prepared in accordance with Examples 1–8 can be used as the active compound in the preparation of the orally administrable formulations of this example.

EXAMPLE 19

Tablet Formulation

This example illustrates the preparation of a representative pharmaceutical formulation containing an active compound of Formula I, e.g., 6-cyclopropylmethyl-8-(3-chlorophenyl)- 1,6-naphthyridine-5-one.

A tablet for oral administration is prepared having the following composition:

| Ingredients | Quantity (mg/tablet) |
|---|---|
| Active compound | 400 |
| corn starch | 50 |
| lactose | 145 |
| magnesium stearate | 5 |

The above ingredients are mixed intimately and pressed into single scored tablets.

Other compounds of Formula I, such as those prepared in accordance with Examples 1–8 can be used as the active compound in the preparation of the tablet formulations of this example.

EXAMPLE 20

Injectable Formulation

This example illustrates the preparation of a representative pharmaceutical formulation containing an active compound of Formula I, e.g., 6-cyclopropylmethyl-8-(3-chlorophenyl)- 1,6-naphthyridine-5-one.

An injectable preparation is prepared having the following composition:

| Ingredients | Quantity |
|---|---|
| Active compound | 0.2 g |
| water (distilled, sterile) | q.s. to 20.0 mL |

Other compounds of Formula I, such as those prepared in accordance with Examples 1–8 can be used as the active compound in the preparation of the injection administrable formulations of this example.

EXAMPLE 21

Suppository Formulation

This example illustrates the preparation of a representative pharmaceutical formulation containing an active compound of Formula I, e.g., 6-cyclopropylmethyl-8-(3-chlorophenyl)- 1,6-naphthyridine-5-one.

A suppository totalling 2.5 grams is prepared having the following composition:

| Ingredients | Quantity |
|---|---|
| Active compound | 500 mg |
| witepsol H-15* | q.s. to 2.5 g |

(*triglycerides of saturated vegetable fatty acid; a product of Riches-Nelson, Inc., New York, N.Y.).

Other compounds of Formula I, such as those prepared in accordance with Examples 1–8 can be used as the active compound in the preparation of the suppository formulations of this example.

While the present invention has been described with reference to the specific embodiments thereof, it should be understood by those skilled in the art that various changes may be made and equivalents may be substituted without departing from the true spirit and scope of the invention. In addition, many modifications may be made to adapt a

What is claimed is:

1. A compound of the formula

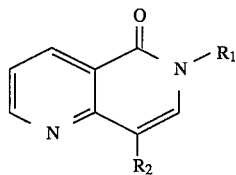

wherein:

$R_1$ is hydrogen, alkyl, lower-alkyl, cycloalkyl, heteroalkyl, heterocycloalkyl, aryl, heteroaryl, cycloalkyl lower-alkyl, heterocycloalkyl lower-alkyl, aralkyl or heteroaralkyl; and $R_2$ is aryl; or a pharmaceutically acceptable salt or N-oxide thereof.

2. A compound of claim 1 wherein $R_2$ is optionally substituted phenyl, or a pharmaceutically acceptable salt or N-oxide thereof.

3. A compound of claim 2 wherein $R_2$ is phenyl substituted with an electron withdrawing group, or a pharmaceutically acceptable salt or N-oxide thereof.

4. A compound of claim 2 wherein $R_2$ is phenyl substituted at the 3-position, or a pharmaceutically acceptable salt or N-oxide thereof.

5. A compound of claim 2 wherein $R_2$ is phenyl optionally substituted with alkyl, methylenedioxy, ethylenedioxy, halo, nitro, trifluoromethyl or cyano, or a pharmaceutically acceptable salt or N-oxide thereof.

6. A compound of claim 2 wherein $R_2$ is phenyl or 3-chlorophenyl, or a pharmaceutically acceptable salt or N-oxide thereof.

7. A compound of claim 2 wherein:

$R_1$ is hydrogen, lower-alkyl, cycloalkyl lower-alkyl, aralkyl or heteroaralkyl, or a pharmaceutically acceptable salt or N-oxide thereof.

8. A compound of claim 7 wherein $R_2$ is phenyl optionally substituted with alkyl, methylenedioxy, ethylenedioxy, halo, nitro, trifluoromethyl or cyano, or a pharmaceutically acceptable salt or N-oxide thereof.

9. A compound of claim 7 wherein $R_2$ is phenyl or 3-chlorophenyl, or a pharmaceutically acceptable salt or N-oxide thereof.

10. A compound of claim 7 wherein $R_2$ is phenyl, or a pharmaceutically acceptable salt or N-oxide thereof.

11. A compound of claim 7 wherein $R_2$ is 3-chlorophenyl, or a pharmaceutically acceptable salt or N-oxide thereof.

12. A compound of claim 10 wherein $R_1$ is ethyl, or a pharmaceutically acceptable salt or N-oxide thereof.

13. A compound of claim 10 wherein $R_1$ is isopropyl, or a pharmaceutically acceptable salt or N-oxide thereof.

14. A compound of claim 10 wherein $R_1$ is cyclopropylmethyl, or a pharmaceutically acceptable salt or N-oxide thereof.

15. A compound of claim 10 wherein $R_1$ is cyclopentylmethyl, or a pharmaceutically acceptable salt or N-oxide thereof.

16. A compound of claim 10 wherein $R_1$ is benzyl, or a pharmaceutically acceptable salt or N-oxide thereof.

17. A compound of claim 10 wherein $R_1$ is 4-pyridylmethyl, or a pharmaceutically acceptable salt or N-oxide thereof.

18. A compound of claim 10 wherein $R_1$ is 2-furanylmethyl, or a pharmaceutically acceptable salt or N-oxide thereof.

19. A compound of claim 10 wherein $R_1$ is 2-thienylmethyl, or a pharmaceutically acceptable salt or N-oxide thereof.

20. A compound of claim 11 wherein $R_1$ is ethyl, or a pharmaceutically acceptable salt or N-oxide thereof.

21. A compound of claim 11 wherein $R_1$ is isopropyl, or a pharmaceutically acceptable salt or N-oxide thereof.

22. A compound of claim 11 wherein $R_1$ is cyclopropylmethyl, or a pharmaceutically acceptable salt or N-oxide thereof.

23. A compound of claim 11 wherein $R_1$ is cyclopentylmethyl, or a pharmaceutically acceptable salt or N-oxide thereof.

24. A compound of claim 11 wherein $R_1$ is benzyl, or a pharmaceutically acceptable salt or N-oxide thereof.

25. A compound of claim 11 wherein $R_1$ is 4-pyridylmethyl, or a pharmaceutically acceptable salt or N-oxide thereof.

26. A compound of claim 11 wherein $R_1$ is 2-furanylmethyl, or a pharmaceutically acceptable salt or N-oxide thereof.

27. A compound of claim 11 wherein $R_1$ is 2-thienylmethyl, or a pharmaceutically acceptable salt or N-oxide thereof.

28. A pharmaceutical composition comprising a pharmaceutically acceptable non-toxic excipient and a therapeutically effective amount of a compound of claim 1, or a pharmaceutically acceptable salt or N-oxide thereof.

29. A method of use of a compound of claim 1, or a pharmaceutically acceptable salt or N-oxide thereof, as an antiinflammatory agent, immunosuppressive agent, anti-allograft rejection agent, anti-graft-vs-host disease agent, anti-allergic agent, anti-asthma agent, anti-rhinitis agent, anti-atopic dermatitis agent, bronchodilation agent, anti-autoimmune disease agent or analgetic agent, by administering to a mammal in need of such treatment a therapeutically effective amount of a compound of claim 1, or a pharmaceutically acceptable salt or N-oxide thereof, to a mammal in need thereof.

* * * * *